(12) United States Patent
Critser et al.

(10) Patent No.: US 8,652,844 B2
(45) Date of Patent: Feb. 18, 2014

(54) METHODS FOR THE CRYOPRESERVATION OF ANIMAL CELLS THAT CONTAIN HIGH LEVELS OF INTRACELLULAR LIPIDS

(75) Inventors: John K. Critser, Columbia, MO (US); Hongsheng Men, Columbia, MO (US)

(73) Assignee: The Curators of the University of Missouri, Columbia, MI (US)

( * ) Notice: Subject to any disclaimer, the term of this patent is extended or adjusted under 35 U.S.C. 154(b) by 900 days.

(21) Appl. No.: 12/304,633

(22) PCT Filed: Jun. 12, 2007

(86) PCT No.: PCT/US2007/013727
§ 371 (c)(1),
(2), (4) Date: Apr. 7, 2010

(87) PCT Pub. No.: WO2007/146253
PCT Pub. Date: Dec. 21, 2007

(65) Prior Publication Data
US 2010/0190248 A1 Jul. 29, 2010

Related U.S. Application Data

(60) Provisional application No. 60/813,273, filed on Jun. 13, 2006.

(51) Int. Cl.
*C12N 5/00* (2006.01)
*C12N 5/02* (2006.01)

(52) U.S. Cl.
USPC .......................... 435/374; 435/325; 435/404

(58) Field of Classification Search
None
See application file for complete search history.

(56) References Cited

U.S. PATENT DOCUMENTS

| | | |
|---|---|---|
| 5,827,741 A | 10/1998 | Beattie et al. |
| 6,500,608 B2 | 12/2002 | Forest et al. |
| 6,503,698 B1 | 1/2003 | Dobrinsky et al. |
| 6,982,272 B2 | 1/2006 | Young et al. |
| 2005/0176827 A1 | 8/2005 | Lee et al. |

*Primary Examiner* — Debbie K Ware
(74) *Attorney, Agent, or Firm* — Maginot, Moore & Beck, LLP

(57) ABSTRACT

A method for cryopreservation of animal cells with high level of intracellular lipid content, comprises the steps of conducting a delipation procedure using one or more lipolytic agent(s) and/or lipogenesis inhibitors during culture of the animal cells to stimulate the hydrolysis of intracellular lipids to reduce the lipid content, and vitrifying the treated animal cells using a modified vitrification solution and a modified warming solution.

15 Claims, 3 Drawing Sheets

FIG. 1

Table 1. Components of modified TL-Hepes.

| Component | mM |
|---|---|
| NaCl | 114.00 |
| KCL | 3.20 |
| NaH$_2$PO$_4$ | 0.34 |
| Na lactate** | 10.00 |
| MgGl$_2$.6H$_2$0 | 0.50 |
| HEPES | 10.00 |
| Na pyruvate | 0.20 |
| Sorbitol | 12.00 |
| NaHCO$_3$ | 2.00 |
| CaCl$_2$.2H$_2$0*** | 2.00 |
| Gentamicin | 25 mg/1000 ml |
| Penicillin C | 65 mg/1000 ml |
| PVA | 0.01% |

FIG. 2

Table 2. *In vitro* survival and hatching ability of vitrified porcine embryos produced *in vitro* after chemical delipation and apoptosis inhibition*.

|  | Vitrification + | | | | Vitrification − | | | |
|---|---|---|---|---|---|---|---|---|
|  | Chemical delipation + | | Chemical delipation − | | Chemical delipation + | | Chemical delipation − | |
|  | Apoptosis Inhibition+ | Apoptosis Inhibition− | Apoptosis Inhibition+ | Apoptosis Inhibition− | Apoptosis Inhibition+ | Apoptosis Inhibition− | Apoptosis Inhibition+ | Apoptosis Inhibition− |
| Blastocysts | 125 (10)* | 52 (5) | 105 (10) | 89 (8) | 43 (5) | 39 (5) | 39 (5) | 73 (8) |
| Full blastocoel | 59 ($47.2 \pm 3.7$)** | 18 ($34.6 \pm 6.7$) | 25 ($23.8 \pm 3.1$) | 13 ($14.6 \pm 4.3$) | 37 ($86.0 \pm 3.9$) | 35 ($89.7 \pm 3.9$) | 37 ($94.9 \pm 4.2$) | 68 ($93.2 \pm 3.1$) |
| Partial blastocoel | 31 | 19 | 26 | 20 | 5 | 4 | 2 | 3 |
| Total survival | 90 ($72.0 \pm 3.7$) | 37 ($71.2 \pm 2.8$) | 51 ($48.6 \pm 5.7$) | 33 ($37.1 \pm 5.1$) | 42 ($97.7 \pm 2.2$) | 39 (100) | 39 (100) | 71 ($97.3 \pm 1.2$) |
| Hatched | 6 ($8.8 \pm 2.9$) | 4 ($7.7 \pm 4.1$) | 2 ($1.9 \pm 1.0$) | 0 (0) | 18 ($41.9 \pm 5.3$) | 19 ($48.7 \pm 5.2$) | 16 ($41.0 \pm 5.9$) | 27 ($37.0 \pm 4.8$) |

*Replicates; **(mean% ± S.E.M).

FIG. 3

Table 3. *In vitro* survival of Vitrified porcine blastocysts after treatment with 10 μM forskolin for 96 hours in culture.

| Forskolin | Total blastocysts | Full blastocoel (%) | Partial blastocoel | Hatched |
|---|---|---|---|---|
| 10 μM | 43 | 26 (60.5)$^a$ | 7(16.3)$^a$ | 6 (14.0)$^a$ |
| 0 μM | 36 | 7 (19.4)$^b$ | 10(27.8)$^a$ | 3 (8.3)$^a$ |

*Different superscripts within a column indicates significant difference ($P < 0.05$, $\chi^2$-test).

METHODS FOR THE CRYOPRESERVATION OF ANIMAL CELLS THAT CONTAIN HIGH LEVELS OF INTRACELLULAR LIPIDS

PRIORITY

This application is a national stage application under 35 U.S.C. 371 based on PCT/US2007/013727, filed Jun. 12, 2007, now expired, which claimed priority to Provisional U.S. Patent Application Ser. No. 60/813,273, filed Jun. 13, 2006, now expired. The entirety of each of these applications are incorporated herein by reference.

FIELD OF INVENTION

The present invention relates to non-invasive methods for increasing the survival of animal cells with high contents of intracellular lipids such as domestic animal oocytes and embryos as well as human adipose cells. Specifically, this invention relates to a non-invasive approach to metabolically reduce intracellular lipids, which are largely responsible for the high sensitivity of cells rich in intracellular lipids to cryopreservation.

BACKGROUND OF INVENTION

Some mammalian reproductive cells that are extremely sensitive to low temperature, such as bovine oocytes and embryos, can be successfully cryopreserved by vitrification at ultra-rapid cooling rates. U.S. Pat. No. 6,500,608 to Forest et al. discloses a method to cryopreserve cells that are highly sensitive to low temperature by vitrification using a loop as a transfer instrument. U.S. Pat. No. 6,982,172 to Yang et al. discloses a method to vitrify oocytes or embryos at ultra-rapid cooling rate by the direct contact of small volume of vitrification solution containing bovine oocytes to the surface of a very cold (−150~180° C.) solid surface with good thermal conductivity. However, cryopreservation of cells with very high levels of intracellular lipids, such as produced porcine embryos, by these approaches does not yield good results.

Intracellular lipid levels are inversely related to cryosurvival of some animal cells. For example, the exceedingly temperature sensitive nature of some domestic animal oocytes and embryos has been proven to be due to their very high level of intracellular lipids. A reduction in the content of intracellular lipids can significantly improve their survival after cryopreservation, a phenomenon that has been well documented in porcine embryos.

Reduction of intracellular lipid contents in porcine embryos is usually accomplished by employing mechanical delipation. The intracellular lipids in porcine embryos are first polarized to one side of embryos by ultracentrifugation. Subsequently, the polarized lipid droplets are removed by micromanipulation. Thus far, this approach has resulted in the best cryosurvival in porcine embryos generated both in vivo and in vitro. However, due to the extensive resources needed, this approach offers very limited practical value. This approach also significantly increases the chance of pathogen transmission because of the damaged zona pellucida after micromanipulation. In addition, it is also extremely labor-intensive and time-consuming.

U.S. Pat. No. 6,503,698 to Dobrinsky and Nagashima discloses a modified mechanical delipation approach applied to the cryopreservation of porcine embryos derived in vivo. In this method, the intracellular lipid droplets are polarized to one side of embryos through centrifugation at a very high speed (13,000 g) and the embryos are then cryopreserved without removal of the polarized lipid droplets. This approach results in a reasonable survival of porcine embryos derived in vivo. However, after cryopreservation, the polarized lipid droplets lose their ability to redistribute into the cytoplasm which may have a detrimental effect on the subsequent development of porcine embryos.

SUMMARY OF INVENTION

The high content of intracellular lipids is the key component that renders mammalian cells rich in intracellular lipids sensitive to low temperatures. It has been demonstrated, at least in porcine embryos, that a reduction in lipid content is correlated with an increased embryo survival during cryopreservation. The present invention provides a method to increase the survival of these cells during cryopreservation through a non-invasive method to reduce their intracellular lipid contents during culture. The application of a lipolytic agent to reduce the lipid content of animal cells represents a novel application of lipolytic agent and a novel approach for delipation in animal cells. The methods of the present invention comprise two steps: the first step is a chemical delipation step employing a lipolytic agent to stimulate the hydrolysis of intracellular lipids in animal cells during culture. The lipid content is reduced as a result of stimulated hydrolysis of intracellular lipids in the presence of lipolytic agent. The potential lipolytic agent used depends on the species from which oocytes or embryos are derived. For example, forskolin is used for the chemical delipation of porcine embryos. Alternatively, lipogenesis inhibitor may be used in combination with lipolytic agents to partially suppress lipogenesis to accelerate the lipid reduction in some cells, e.g. adipocytes.

The second step of the method is a cryopreservation step employing either slow cooling (adipocytes) or vitrification (oocytes and embryos). In one embodiment, a vitrification method described previously by Vajta et al., in Mol Reprod Dev 51:53-58, 1998, the disclosure of which is incorporated herein by reference, is used with modifications to vitrify the oocytes or embryos. The major modifications to this known vitrification procedure includes use of a modified vitrification solution and a modified warming solution, both specifically designed to fully exploit the benefits of the novel delipation method described herein.

BRIEF DESCRIPTION OF THE DRAWINGS

FIG. 1 shows a table displaying the contents of modified TL-Hepes according to at least one embodiment herein.

FIG. 2 shows a table displaying the in vitro survival and hatching ability of vitrified porcine embryos produced in vitro after chemical deligation and apoptosis inhibition.

FIG. 3 shows a table displaying the in vitro survival of vitrified porcine blastocysts after treatment with forskolin for 96 hours in culture.

DETAILED DESCRIPTION OF THE PREFERRED EMBODIMENTS

Specific language is used to describe several embodiments of this invention to promote an understanding of the invention and its principles. It must be understood that no specific limitation of the scope of this invention is intended by using this specific language. Any alteration and further modification of the described methods or devices, and any application of the principle of this invention are also intended that normally occur to one skilled in this art.

One objective of the present invention is to provide a novel protocol for the reduction of intracellular lipids through a non-invasive method to thereby increase the cryosurvival of mammalian cells rich in intracellular lipids, especially oocytes and embryos. This protocol takes advantage of the lipolytic property of lipolytic agents for the purpose of lipid reduction in animal cells rich in intracellular lipids. This reduction is achieved using one or more lipolytic agents to stimulate the hydrolysis of intracellular lipids in animal cells during culture. Some lipogenesis inhibitors may also be used to partially inhibit the synthesis of intracellular lipids in order to reduce the level of intracellular lipids in these cells.

Lipid hydrolysis is a hormone-controlled process. The endogenous hormone-sensitive lipase that catalyzes the hydrolysis of intracellular lipids is regulated by the levels of various hormones. Catecholamines, adrenocorticotropic Hormone (ACTH), and glucagons stimulate the activity of cellular endogenous lipase, while insulin and melatonin attenuate its activity. During normal physiological processes, stimulatory hormones bind to their receptors on cell membrane and subsequently activate adenylate cyclase. Increased cAMP as a result of adenylate cyclase activation leads to the activation of cAMP-dependent protein kinases and subsequently to activation of lipases through phosphorylation. The activated lipase translocates from the cytoplasm to the lipid droplet and catalyzes the enzymatic hydrolysis of intracellular lipids. The primary target of lipase is triacylglycerols which are hydrolyzed into fatty acids and glycerol. Activated lipase also catalyzes the hydrolysis of diacylglycerols, monoacylglycerols, cholesteryl esters and other lipids.

Suitable lipolytic agents include epinephrine, norepinephrine, isoproterenol, 7β-acetoxy-8,13-epoxy-1α,6β,9α-trihydroxy-labd-14-ene-11-one (forskolin), dibutyryl cyclic AMP (DBcAMP) and theophylline. These agents have the capability to stimulate intracellular lipolysis by acting on different components of the lipolytic pathway. Manipulation of intracellular lipolysis in cultured adipose cells or in cell-free systems using these lipolytic agents has been widely used in the field of lipid research over several decades to study various aspects of lipid metabolism, such as the signal transduction of lipid metabolism, the physiological roles of lipase and the pathology of dysregulation of lipolytic reactions in various species. U.S. Pat. No. 4,525,395 to Greenway et al., discloses a method for selective weight control of humans employing delivery of lipolytic agents (theophylline, isoproterenol, forskolin and epinephrine) to the selected areas of the body through injection, implantation, or topical application, to stimulate β-adrenergic receptors and stimulating the hydrolysis of lipids in adipocytes in targeted areas. It has been demonstrated that this intervention with lipolytic agent to selected regions with excessive fat deposit accelerates weight reduction from these regions. U.S. Pat. No. 4,588,724 to Greenway et al. discloses a similar approach employing α-2 adrenergic receptors to block the inhibition of lipolysis. U.S. Pat. No. 5,507,790 to Weiss also discloses an approach for selective weight loss employing radiant energy-producing electromedical apparatus together with local topically applied lipolytic agents to accelerate local tissue lipolysis. Local fat loss occurs as a result of local cell temperature elevation and local fat cell lipolysis.

The protocol according to the present invention exploits the lipolytic property of lipolytic agents to reduce the intracellular lipid contents of animal cells prior to cryopreservation. Suitable cells include oocytes, embryos and human adipose cells. In accordance with the invention, lipolysis is achieved utilizing the lipolytic agent for the reduction of intracellular lipids in animal cells. The treated cells with a lower level of intracellular lipids are then cryopreserved by either slow cooling (human adipose cells) or vitrification at ultra-rapid cooling rate (oocytes and embryos). In one embodiment, the ultra-rapid cooling rate is achieved employing minimal amount of vitrification solution and direct plunging into liquid nitrogen.

Reduction of intracellular lipids may also be achieved by inhibition of lipogenesis. Lipids serve numerous functions in animal cells and are key components of cell membranes and membranes of subcellular organelles. Therefore, complete inhibition of lipogenesis is lethal to cells. Several potent lipid synthesis inhibitors, such as luteolin, quercetin, kaempferol, have been used to treat cancer by inducing apoptosis through lipid synthesis inhibition in cancer cells. Some potent lipogenesis inhibitors have also been used as herbicides, such as aryloxyphenoxypropionates and cyclohexanediones. These chemicals inhibit lipogenesis through inhibition of acetyl CoA carboxylase, resulting in cell death. Therefore, it is believed that potent lipogenesis inhibitors are not suitable for the methods of the present invention. However, some agents, such as triacsin C and niacin, show moderate lipogenesis inhibitory activity. These less potent agents may provide some beneficial effects on the reduction of intracellular lipids without significantly affecting cell division as lipid synthesis is required.

Some animal cells have a very high level of intracellular lipid contents, such as oocytes and embryos from domestic species, which cause the cells to exhibit significant sensitivity to low temperature. One common approach for the cryopreservation of oocytes and embryos with an extremely temperature-sensitive nature is to vitrify at an ultra-rapid cooling rate. This may be achieved by decreasing the volume of vitrification solution in the range of 2-0.1 μl. Although in some approaches the volume of vitrification solution has been reduced to the lowest volume possible, some cells, such as porcine embryos produced in vitro, are still a challenge to cryopreserve with these approaches.

Lipids are a major source of intracellular energy reserve and major structural component of cell membrane in mammalian species. They are especially rich in oocytes and early embryos of some domestic species, such as cattle and swine, and in adipose cells. There are several explanations for the detrimental effects of intracellular lipids during cryopreservation. For example, intracellular lipids may become toxic to oocytes or embryos after cryopreservation as a result of increased peroxidation. Another possible reason is that lipids may also become unusable for oocytes or embryos as a result of irreversible changes or induction of heterogeneous intracellular ice formation. Therefore, a reduction of the lipid contents will increase the cryosurvival of oocytes or embryos rich in intracellular lipids as well as adipose cells.

In one prior procedure, lipids were removed prior to cryopreservation of porcine embryos. The first step in this procedure was to polarize intracellular lipids by centrifuging embryos at a high speed (13,000 g), followed by removal of the polarized lipid drops by micromanipulation. However, due to the damage to the zona pellucida during micromanipulation, the chance of pathogen transmission in this procedure is significantly increased. In addition, due to the extensive resources needed, this approach offers very limited practical value. It is also extremely labor-intensive and time-consuming. The present invention addresses these short-comings by utilizing a novel approach to reduce the lipid content in animal cells by stimulating the hydrolysis of intracellular lipids employing lipolytic agents, such as epinephrine, norepinephrine, isoproterenol, forskolin, DBcAMP and theophylline.

The signal transduction pathway of intracellular lipolysis consists of adrenergic receptors, adenylate cyclase, cAMP, protein kinase A, and lipase. Lipolytic signal transduction starts with the binding of hormone to adrenergic receptors on cell membrane. After hormone binds to membrane receptors, adenylate cyclase, which is closely associated with the receptors, is activated and then catalyzes the production of cAMP from ATP. Intracellular lipase is activated by a rise in intracellular cAMP concentration and the activated lipase catalyzes the hydrolysis of triacylglycerols which are hydrolyzed into fatty acids and glycerol. Activated lipase also catalyzes the hydrolysis of diacylglycerols, monoacylglycerols, cholesteryl esters and other lipids.

According to one aspect of the invention, reduction of intracellular lipids through stimulated lipolysis in animal cells rich in lipids is accomplished by culturing these cells with optimal concentration of lipolytic agent of choice for a period of time. Lipolytic agents, such as epinephrine, norepinephrine, isoproterenol, forskolin, DBcAMP and theophylline, are capable of acting on different components of lipolytic signal transduction pathway and stimulating the hydrolysis of intracellular lipids. Epinephrine, norepinephrine and isoproterenol act as β-agonists and bind to adrenergic receptors on the surface of target cells. Forskolin acts directly on adenylate cyclase and activates its activity. DBcAMP works in a similar way of cAMP and activates protein kinase A. Theophylline exerts its lipolytic effect through antagonism of adenosine A1 receptor as well as phosphodiesterase inhibition. In a further step of the invention, the treated oocytes or embryos are subject to vitrification at an ultra-rapid cooling rate. Treated adipose cells are subject to controlled slow cooling.

The major pathway of lipid synthesis is the glycerol phosphate pathway. Lipid synthesis is initiated by the formation of Acyl-CoA from fatty acid by the activity of acyl-CoA synthetase. Acyl-CoAs are then sequentially incorporated into glycerol-3-phosphate by three acyltransferases: glycerol-3-phosphate acyltransferase, 1-acylglycerol-3-acyltransferase, diacylglycerol acyltransferase to form triacylglycerol.

Reduction of intracellular lipids may also be accomplished by culturing these cells with optimal concentration of inhibitors with moderate ability of lipid synthesis inhibition. Some lipogenesis inhibitors, such as triacsin C, niacin, are able to partially inhibit the synthesis of intracellular lipids through different mechanisms. Triacsin C inhibits the synthesis of lipids through inhibiting the activity of long-chain acyl-CoA synthetase. Niacin inhibits triacylglycerol synthesis by suppressing the activity of diacylglycerol acyltransferase.

According to one specific embodiment, cryopreservation of oocytes or embryos commences by first exposing the oocytes or embryos to an equilibration medium for 20 min. The equilibration medium is made of 1.625 M glycerol in a modified TL-Hepes (mTL-Hepes, See, Table 1 in FIG. 1) with 20% (v/v) fetal bovine serum (FBS) and 20 µM benzyloxycarbonyl-Val-Ala-Asp-fluoromethyl ketone (Z-VAD-FMK, an inhibitor to inhibit the initiation of apoptosis) supplementations. After equilibration, oocytes or embryos, in a group of five, are then sequentially exposed to two 30 µL droplets of vitrification solution consisting of 6.5 M glycerol, 20% FBS and 20 µM Z-VAD-FMK in mTL-Hepes and quickly mixed by pipetting. Within 30-45 seconds of exposure to VS, blastocysts were loaded into the tip of an open pulled straw (OPS) with 1-2 µL of VS and plunged directly into liquid nitrogen ($LN_2$). Blastocysts were stored in $LN_2$.

Vitrified blastocysts are warmed at 25° C. in an mTL-Hepes solution containing 1 M sucrose, 20% FBS and 20 µM Z-VAD-FMK. After 5 minutes in the 1 M sucrose solution, blastocysts were exposed sequentially to 0.5 M, 0.25 M, 0 M, 0 M sucrose solutions in mTL-Hepes with 20% FBS for 5 minutes each.

For equilibrium cooling of human adipose cells, treated adipose cells are pelleted through centrifugation and are then subjected to freezing. Cryopreservation of human adipocytes is conducted according to a known method.

EXAMPLES

The following examples will serve to illustrate the application of the present invention.

Example 1

Cryopreservation of In Vitro Produced Porcine Embryos

A. Production and Delipation of In Vitro Produced (IVP) Porcine Blastocysts

Immature sow oocytes were purchased from BOMED Inc (Madison, Wis., USA) delivered in a commercial shipper overnight in a maturation medium (TCM199-based maturation medium). After 42-44 hours of maturation, matured oocytes were fertilized and cultured in a known manner. On Day 4 (fertilization=Day 0) of embryo culture, the culture medium was supplemented with 10% FBS. On Day 5, a portion of the embryos was treated with 10 µM forskolin. Embryos without forskolin treatment served as controls. After 24 hours of forskolin treatment, blastocysts and expanded blastocysts of excellent quality were used for the vitrification.

B. Vitrification of IVP Porcine Blastocysts

Blastocysts were vitrified using a known OPS method. A vitrification solution (VS) and a known pre-vitrification treatment procedure were used. Briefly, blastocysts were equilibrated with 1.625 M glycerol in a modified TL-Hepes (mTL-Hepes) with 20% (v/v) FBS and 20 µM Z-VAD-FMK for 20 minutes at 25° C. Blastocysts, in a group of five, were then sequentially exposed to two 30 µL droplets of VS consisting of 6.5 M glycerol, 20% FBS and 20 µM Z-VAD-FMK in mTL-Hepes and quickly mixed by pipetting. Within 30-45 seconds of exposure to VS, blastocysts were loaded into the tip of OPS with 1-2 µL of VS and plunged directly into liquid nitrogen ($LN_2$). Blastocysts were stored in $LN_2$ for 22-24 h. Vitrified blastocysts were warmed at 25° C. in an mTL-Hepes solution containing 1 M sucrose, 20% FBS and 20 µM Z-VAD-FMK. After 5 minutes in the 1 M sucrose solution, blastocysts were exposed sequentially to 0.5 M, 0.25 M, 0 M, 0 M sucrose solutions in mTL-Hepes with 20% FBS and 20 µM Z-VAD-FMK for 5 minutes each. The developmental potential of warmed blastocysts were either assessed in vitro by their ability to recover to their original shape and to hatch during culture or transferred into recipient females, as shown in Table 2 of FIG. 2.

Example 2

Cryopreservation of Porcine Embryos after Chemical Delipation for Extended Hours Porcine embryos were produced in vitro as Example 1, except that 10 µM forskolin was supplemented into culture medium on Day 2 (fertilization=Day 0) of embryonic development. Day 6 porcine blastocysts were vitrified and warmed as described in Example 1 without the supplementation of apoptosis inhibitor. The results are shown in Table 3 of FIG. 3.

Example 3

Cryopreservation of Porcine Oocytes

Similar to porcine embryos, porcine oocytes also contain a very high level of intracellular lipids. The high sensitivity to low temperature of porcine oocytes is also due to their high intracellular lipid content. In accordance with one embodiment of the invention, a delipation approach involving the use of lipolytic agents to stimulate the lipolysis in porcine oocytes will be used to increase the cryosurvival of porcine oocytes. Immature porcine oocytes will be collected from abattoir ovaries and matured. For reduction of intracellular lipids, lipolytic agent will be supplemented into maturation medium to facilitate the enzymatic hydrolysis of intracellular lipids. After maturation and delipation, oocytes will be vitrified. Developmental potential of vitrified oocytes will be assessed by their developmental ability both in vitro and in vivo after in vitro fertilization and culture.

Example 4

Cryopreservation of Bovine Oocytes

Bovine oocytes are exceedingly sensitive to low temperature. The high level of intracellular lipids is probably responsible for this sensitivity. There is evidence that intracellular lipids may contribute to the cryosensitivity of bovine oocytes and early embryos because removal of intracellular lipids through centrifugation and micromanipulation improves the cryosurvival of bovine embryos. According to the present invention, the intracellular lipids of bovine oocytes will also be reduced employing a chemical delipation approach. Immature bovine oocytes will be isolated from abattoir ovaries and matured. Selected lipolytic agent (epinephrine, norepinephrine, isoproterenol, forskolin, DBcAMP or theophylline) will be supplemented into maturation medium with optimal concentration to stimulate the hydrolysis of intracellular lipids and consequently reduce the intracellular level in bovine oocytes. After 24 hours of maturation, oocytes will be vitrified and warmed using known procedures.

Example 5

Cryopreservation of Bovine Early Stage Embryos

Bovine early stage embryos ranging from zygotes to morulae contain high levels of intracellular lipids that are at least partly responsible for their high sensitivity to cryopreservation. Lipid removal by centrifugation and micromanipulation is known to significantly increase the cryosurvival of early stage bovine embryos. However, in accordance with a further embodiment of the invention, the chemical delipation approach will also be used to reduce the lipid content in bovine early stage embryos in order to increase their cryosurvival. Bovine early stage embryos will be produced by in vitro maturation, fertilization and culture of immature oocytes from ovaries obtained from abattoir. During specific stage of development, one lipolytic agent will be chosen from the following lipolytic agents: epinephrine, norepinephrine, isoproterenol, forskolin, DBcAMP or theophylline, and will be supplemented into embryo culture medium with optimal concentration to stimulate the hydrolysis of intracellular lipids and consequently reduce the intracellular level in bovine embryos. After delipation treatment, embryos will be vitrified and warmed using known procedures.

Example 6

Cryopreservation of Dog Oocytes

The ability to cryopreserve dog oocytes will contribute to the conservation of dog breeds and as well as wild canines considered to be endangered (Convention on International Trade in Endangered Species of Wild Flora and Fauna, part of the Endangered Species Act, 1973, Code Fed Reg., part 23). Dog oocytes also contain a very high level of intracellular lipids. Therefore, reduction in intracellular lipids may also increase their cryotolerance.

The chemical delipation approach of the present invention will be used to reduce the lipid content in dog oocytes. Lipolytic agent of choice will be added to dog oocyte maturation medium to stimulate their lipolysis during maturation. After delipation treatment, embryos will be vitrified and warmed using procedures previously described.

Example 7

Cryopreservation of Cat Oocytes

Similar to the cryopreservation of dog oocytes, cat oocyte cryopreservation will also contribute to the conservation of different breeds of domestic cats as well as the conservation of wild feline species, from which 37 are considered to be endangered. Cat oocytes also contain a very high level of intracellular lipids that makes their cryopreservation problematic.

The chemical delipation approach of the present invention will be used to reduce the lipid content in cat oocytes. Lipolytic agent of choice will be added to cat oocyte maturation medium to stimulate their lipolysis during maturation. After chemical delipation, embryos will be vitrified and warmed using procedures previously described.

Example 8

Cryopreservation Human Adipose Cells

A method to cryopreserve human adipose cells is needed due to the increasing popularity of plastic surgery. This technology will benefit patients who receive a fat injection, a procedure that needs repeated injection every 6 to nine months. However, adipocytes are very sensitive to cryopreservation and conventional slow cooling resulted in very poor post-thaw survival. The cryosensitivity of adipocytes is most likely due to their high intracellular lipid content. Therefore, a reduction in their intracellular lipid level will increase their post-thaw survival.

According to the present invention, human adipocytes will be collected from liposuction and digested into single cell suspension using collagenase and concentrated through centrifugation. Adipocytes will then be cultured in human adipocyte culture medium supplemented with an optimal concentration of one of the lipolytic agents (epinephrine, norepinephrine, isoproterenol, forskolin, DBcAMP and theophylline) and/or one of the lipogenesis inhibitors, triacsin C and niacin. After a certain period of culture, adipose cells will be pelleted through centrifugation, and pelleted adipose cells will then be subjected to freezing. Cryopreservation of human adipocytes will be conducted according to known methods.

Example 9

Cryopreservation Mussel Oocytes

Cryopreservation of mussel oocytes will increase the efficiency of breeding by preserving genetically superior lines and selective breeding. Cryopreservation can also reduce production costs in hatcheries by enabling year-round juvenile (spat) production, independent of mature broodstock. However, cryopreservation of mussel oocytes of any breeds still remains challenging.

Female mussels store high amount of lipids in oocytes which may contribute to the cryosensitivity of mussel oocytes. Therefore, reduction of intracellular lipids with lipolytic agents may improve the cryotolerance of mussel oocytes. For lipolytic treatment, mussel oocytes will be co-cultured with lipolytic agent of choice for a period of time. Treated mussel oocytes will be cryopreserved using a known equilibrium approach.

What is claimed is:

1. A method for cryopreservation of animal cells with high level of intracellular lipid content, comprising:
    conducting a delipation procedure, the delipation procedure comprising the steps of providing one or more animal cells to a culture media, and further comprising the step of providing one or more lipolytic agent(s) and/or lipogenesis inhibitors to the culture media to stimulate the hydrolysis of intracellular lipids to reduce the lipid content; and
    vitrifying the treated animal cells using a vitrification solution and a warming solution.

2. The method of claim 1, wherein the cells are human adipocytes.

3. The method of claim 1, wherein the cells are oocytes rich in intracellular lipids.

4. The method of claim 1, wherein the cells are embryos rich in intracellular lipids.

5. The method of claim 1, wherein the lipolytic agent is epinephrine.

6. The method of claim 1, wherein the lipolytic agent is norepinephrine.

7. The method of claim 1, wherein the lipolytic agent is isoproterenol.

8. The method of claim 1, wherein the lipolytic agent is forskolin.

9. The method of claim 1, wherein the lipolytic agent is dibutyryl cyclic AMP (DBcAMP).

10. The method of claim 1, wherein the lipolytic agent is theophylline.

11. The method of claim 1, wherein the lipogenesis inhibitor is triacsin C.

12. The method of claim 1, wherein the lipogenesis inhibitor is niacin.

13. The method of claim 1, wherein the vitrification solution consists of 6.5 M glycerol, 20% FBS and 20 µM benzyloxycarbonyl-Val-Ala-Asp-fluoromethyl ketone (Z-VAD-FMK, a caspase inhibitor) in TL-Hepes.

14. The method of claim 1, wherein the warming solution consists of 1 M sucrose, 20% FBS and 20 µM Z-VAD-FMK in mTL-Hepes.

15. The method of claim 14, further comprising subsequent rehydration using the same warming solution with descending concentrations of sucrose at about 0.5 M and 0.25 M, respectively.

* * * * *